United States Patent
Hionidi et al.

(10) Patent No.: US 12,336,979 B2
(45) Date of Patent: *Jun. 24, 2025

(54) MATERIAL AND METHOD FOR TREATING CANCER

(71) Applicant: UroGen Pharma Ltd., Ra'anana (IL)

(72) Inventors: Yulia Hionidi, Petah Tiqwa (IL); Omer Tsipori, Sha'ar Efraim (IL); Marina Konorty, Hertzeliya (IL)

(73) Assignee: UroGen Pharma Ltd., Ra'anana (IL)

( * ) Notice: Subject to any disclaimer, the term of this patent is extended or adjusted under 35 U.S.C. 154(b) by 359 days.

This patent is subject to a terminal disclaimer.

(21) Appl. No.: 17/546,204

(22) Filed: Dec. 9, 2021

(65) Prior Publication Data

US 2022/0202773 A1 Jun. 30, 2022

Related U.S. Application Data

(60) Provisional application No. 63/124,111, filed on Dec. 11, 2020.

(51) Int. Cl.
| | |
|---|---|
| *A61K 31/407* | (2006.01) |
| *A61K 9/06* | (2006.01) |
| *A61K 47/10* | (2017.01) |
| *A61K 47/18* | (2017.01) |
| *A61K 47/38* | (2006.01) |

(52) U.S. Cl.
CPC .............. *A61K 31/407* (2013.01); *A61K 9/06* (2013.01); *A61K 47/10* (2013.01); *A61K 47/18* (2013.01); *A61K 47/38* (2013.01)

(58) Field of Classification Search
CPC ........ A61K 31/407; A61K 9/06; A61K 47/10; A61K 47/18
See application file for complete search history.

(56) References Cited

U.S. PATENT DOCUMENTS

| | | |
|---|---|---|
| 6,286,513 B1 | 9/2001 | Au et al. |
| 6,482,435 B1 | 11/2002 | Stratton et al. |
| 7,723,085 B2 | 5/2010 | Smith et al. |
| (Continued) | | |

FOREIGN PATENT DOCUMENTS

| | | |
|---|---|---|
| EP | 0386960 A2 | 9/1990 |
| WO | WO2011089604 A2 | 7/2011 |
| (Continued) | | |

OTHER PUBLICATIONS

Calderon, C. P.; Daniels, A. L.; Randolph, T. W. "Deep Convolutional Neural Network Analysis of Flow Imaging Microscopy Data to Classify Subvisible Particles in Protein Formulations" Journal of Pharmaceutical Sciences 107 (2018) 999-1008 (Year: 2018).*

(Continued)

*Primary Examiner* — John S Kenyon
*Assistant Examiner* — John D McAnany
(74) *Attorney, Agent, or Firm* — VENABLE LLP

(57) ABSTRACT

A kit provides for sustained release of therapeutic agents for local treatment of cancer diseases by providing lyophilized Mitomycin C in a slowly releasing biocompatible hydrogel to be applied to affected tissue. The hydrogel comprises (Continued)

Mechanical resistance of composition G and E to a constant shear stress poloxamer 407, hydroxypropylmethylcellulose and water. A lyophilized composition comprises mitomycin C and urea as a bulking agent.

6 Claims, 1 Drawing Sheet

(56) References Cited

U.S. PATENT DOCUMENTS

| | | | |
|---|---|---|---|
| 9,040,074 B2 * | 5/2015 | Holzer | A61P 13/02 |
| | | | 424/434 |
| 9,801,854 B1 * | 10/2017 | Strauss-Ayali | A61K 47/10 |
| 9,950,069 B2 * | 4/2018 | Holzer | A61P 1/16 |
| 10,039,832 B2 * | 8/2018 | Holzer | A61K 38/2013 |
| 10,471,150 B2 | 11/2019 | Konorty et al. | |
| 2004/0009212 A1 | 1/2004 | Tsai | |
| 2007/0275110 A1 | 11/2007 | Dott et al. | |
| 2009/0142259 A1 | 6/2009 | Gao et al. | |
| 2009/0214685 A1 | 8/2009 | Hunt | |
| 2010/0015200 A1 | 1/2010 | McClain et al. | |
| 2013/0046275 A1 | 2/2013 | Holzer et al. | |
| 2014/0105884 A1 | 4/2014 | Konorty et al. | |
| 2014/0142191 A1 | 5/2014 | De La Zerda et al. | |
| 2015/0366974 A1 | 12/2015 | Holzer et al. | |
| 2016/0256391 A1 * | 9/2016 | Schuldt-Lieb | A61K 9/1623 |
| 2017/0112935 A1 | 4/2017 | Holzer et al. | |
| 2017/0128424 A1 | 5/2017 | Rothstein | |
| 2017/0136127 A1 | 5/2017 | Maki et al. | |
| 2017/0143833 A1 | 5/2017 | De La Zerda et al. | |
| 2019/0201334 A1 * | 7/2019 | Hakim | A61P 35/00 |
| 2020/0114008 A1 | 4/2020 | Konorty | |
| 2022/0118096 A1 | 4/2022 | Konorty | |
| 2023/0233685 A1 | 7/2023 | Holzer et al. | |
| 2023/0241220 A1 | 8/2023 | Holzer et al. | |
| 2023/0241221 A1 | 8/2023 | Holzer et al. | |

FOREIGN PATENT DOCUMENTS

| | | |
|---|---|---|
| WO | WO2013011504 A1 | 1/2013 |
| WO | 2018/169960 A1 | 9/2018 |
| WO | WO2022123480 A1 | 6/2022 |

OTHER PUBLICATIONS

Rey-Rico, A.; Cucchiarini, M. "PEO-PPO-PEO Tri-Block Copolymers for Gene Delivery Applications in Human Regenerative Medicine—An Overview" Int. J. Mol. Sci. 19, 775; doi:10.3390/ijms 19030775, 2018. (Year: 2018).*

International Search Report for International Patent Application No. PCT/IB2021/061499, mailed on Feb. 23, 2022.

Written Opinion of the International Searching Authority for International Patent Application No. PCT/IB2021/061499, mailed on Feb. 23, 2022.

H.T. Ta, et al., "Injectable chitosan hydrogels for localised cancer therapy", Journal of Controlled Release, vol. 126, pp. 205-216 (2008).

Y. You, et al., "Intraoperative Mitomycin C in Dacryocystorhinostomy", Opthalmic Plastic and Reconstructive Surgery, vol. 17, No. 2, pp. 115-119 (2001).

H. Wang, U.S. Pharmacopeia, http://www.pharmacopeia.cn/v29240/usp29nf24s0_m66210.html, vol. 29, No. 6, p. 2020 (2007), retrieved from the internet on Feb. 21, 2024.

X. Gao, et al., "Bladder Tissue Uptake of Mitomycin C during Intravesical Therapy is Linear with Drug Concentration in Urine", Clinical Cancer Research, vol. 3, pp. 139-143 (1998).

T.D. Schmittgen, et al., "Pharmacodynamics of Mitomycin C in Cultured Human Bladder Tumors", Cancer Research, vol. 51, pp. 3849-3856 (1991).

Technical Bulletin, Pluronic Block Copolymer NF Grades (Poloxamer NF Grades), BASF The Chemical Company, 2 pages (2002).

S. Miyazaki, et al., "Antitumor Effect of Pluronic F-127 Gel Containing Mitomycin C on Sarcoma-180 Ascites Tumor in Mice", Chem. Pharm. Bull. 40(8) 2224-2226 (1992).

E. Bilensoy, et al., "Mucoadhesive, Thermosensitive, Prolonged-Release Vaginal Gel for Clotrimazole: beta-Cyclodextrin Complex", AAPS PharmSciTech 2006; 7(2) Article 38 (http://www.aapspharmscitech.org).

JELMYTO (mitomycin) [package insert]. Princeton, NJ: UroGen Pharma, Inc; Apr. 2020.

* cited by examiner

Mechanical resistance of composition G and E to a constant shear stress
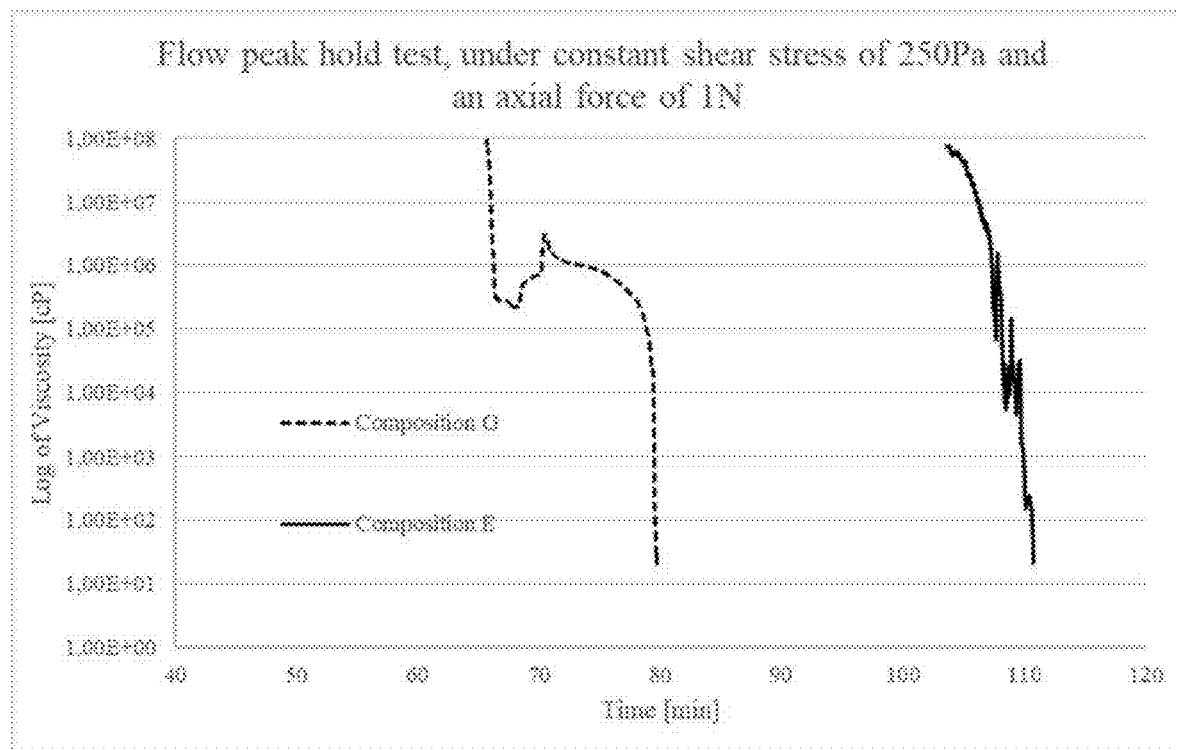

MATERIAL AND METHOD FOR TREATING CANCER

FIELD OF THE INVENTION

The invention relates in general to pharmaceutical compositions, means and methods for sustained release of therapeutic agents for local treatments. It relates in particular to means and methods for local treatment of cancer diseases by embedding lyophilized Mitomycin C in a slowly releasing biocompatible hydrogel applied to affected tissue.

BACKGROUND OF THE INVENTION i. Topical/Local Treatment of Diseases

Methods by which a drug is delivered can have a significant effect on its efficacy. In many cases, the drug is introduced systemically into the blood system, which then delivers it via the blood stream throughout the body. This form of access is broadly termed systemic treatment. In other cases, a more targeted delivery can focus the therapeutic effect onto the target organ, providing therapeutic benefits and avoiding side effects. Some drugs have an optimum concentration range within which maximum benefit is derived, and concentrations above or below this range can be toxic or produce no therapeutic benefit at all. In the context of the present invention, treatments that effect specific tissues or organs by directly accessing them are termed topical or local treatments, as opposed to systemic treatments that were described above. Sustained release of a drug may involve polymers that typically release the drug at a controlled rate due to diffusion out of the polymer or by dilution of the polymer over time. Topical administration of drugs may change the rate or concentration at which drugs enter the tissue and the pharmacokinetics of the drug, thus the correctly designed materials can optimize the therapeutic effect by increasing drug level or controlling the drug release rate.

ii. Topically Administered Drugs

Among the drugs that can be administered topically are drugs that belong to the following families:
1. Antineoplastic drugs
2. Chemotherapeutic agents
3. Anti-infective agents (e.g. Antimicrobial drugs, Antiparasitic agents, Antivirals))
4. Genito-urinary system drugs
5. Anti-inflammatory products
6. Analgesics
7. Musculoskeletal system acting drugs
8. Drugs acting on the blood and blood forming organs (Antihemorrhagics, Antithrombotic agents, antianemic drugs)
9. Dermatologic drugs (antifungals, antiseptic)
10. Gastrointestinal system (antiobesity, acid related disorders)

The specific values of cavity characteristics require careful consideration in the development of topical drugs suitable for treatment of diseases inside these cavities.

iii. Chemotherapy—Anticancer Drugs—Mitomycin C

Many chemotherapy (antineoplastic) drugs used as cancer treatments bind to DNA, resulting in synthesis inhibition and strand breakage. It has been known that in some intravesical instillations, chemotherapy drugs are administered at dose concentrations of around 1 mg/ml for 1-2 hour sessions.

In the particular case of treatment of bladder cancer, the bladder tissue penetration by chemotherapy drugs—a critical parameter in treatment effectiveness—exhibits a linear relationship with the concentration of the chemotherapy drugs (see Gao X, Au J L, Badalament R A, Wientjes M G. Bladder tissue uptake of mitomycin C during intravesical therapy is linear with drug concentration in urine. Clin Cancer Res. 1998 January; 4(1):139-43)). Furthermore, chemotherapy drug penetration is higher in the tumor tissue than in the adjacent normal urothelium. Gao et al demonstrated double Mitomycin C (MMC) concentration in tissue when installing 40 mg/20 ml as compared with 20 mg/20 ml MMC: human bladder tumors had a significantly higher tissue uptake of MMC than the normal bladder tissue.

The anti-tumor effect of chemotherapy drugs depends on concentration and exposure time. Schmittgen et al (see Schmittgen T D, Wientjes M G, Badalament R A, Au J L. Pharmacodynamics of mitomycin C in cultured human bladder tumors. Cancer Res. 1991 Aug. 1; 51(15):3849-56) demonstrated, both in TCC cell cultures and human bladder tumor tissue cultures, that a higher concentration was needed in order to get a similar cell kill effect when exposure time to MMC was reduced.

The proven conclusion is that maintaining optimal drug concentration (therapeutic effect) for longer treatment duration will enhance the treatment efficacy.

iv. Required Properties for Topical Treatment in the Bladder and Other Internal Cavities One approach to treatment of diseases of internal body cavities such as the bladder is topical application of a therapeutic agent entrained in a suitable composition. Such a compositions requires one or more of the following properties:

- Suitable rheological properties (viscosity, thixotropy, G', G")—required for the introduction of the material into the internal cavity
- Adhesion—to enhance drug delivery
- Mechanical properties to provide sufficient flexibility—to comply with the volume and shape natural changes of the internal cavity under treatment
- Biocompatibility
- Duration of time that the composition remains in the internal cavity or within the solid tumor before it completely dissolve/degrades
- Increased drug bioavailability, but without increasing toxicity
- A suitable Active Pharmaceutical Ingredient (API)—the medical drug or drug derivative chosen from the drugs that known for the use as a topical/local active ingredient
- Favorable loading of drug or API in the hydrogel. For certain clinical protocol the amount and concentration of the drug or API mixed into the hydrogel have to be set to a prescribed level.
- The ability of the hydrogel to release the drug in a controlled manner such that the actual drug concentration vis-à-vis the organ tissue or lining upon which the mixture will be optimal for each treatment. It is precisely the specific composition of the mixture that determines the release profile of the drug and its adsorption into the target tissue. For example the addition of certain agents in given concentrations to provide increase loading capacity of the composition or easier enhanced absorption by the internal organ lining.
- Drug viability. The hydrogel is designed and tested not to reduce the viability duration of the drug or API that is mixed into it, so that the amount that is released throughout the treatment will have the optimal therapeutic effect.

v. Limitations of Superficial Bladder Cancer (SBC) Treatments Known in the Art

SBC is a highly-recurrent form of cancer. To lower recurrence, it is considered necessary to treat patients with a single intravesical chemotherapy instillation immediately after Transurethral Resection of Bladder Tumor (TUR-BT).

A meta-analysis of 7 randomized trials (1,476 patients with a median follow-up of 3.4 years) has demonstrated that one chemotherapy instillation immediately after Tumor resection (TUR) decreases the relative risk of recurrence by 40% (see Sylvester R J, Oosterlinck W, van der Meij den A P. A single immediate postoperative instillation of chemotherapy decreases the risk of recurrence in patients with stage Ta T1 bladder cancer: a meta-analysis of published results of randomized clinical trials. J Urol. 2004 June; 171(6 Pt 1):2186-90). The timing of the instillation is crucial: in all studies, instillation was administered within 24 hours. A study reported that if the first instillation was not given within 24 hours, the risk of recurrence increased twofold (see Kaasinen E, Rintala E, Hellström P, Viitanen J, Juusela H, Raj ala P, Korhonen H, Liukkonen T; FinnBladder Group. Factors explaining recurrence in patients undergoing chemoimmunotherapy regimens for frequently recurring superficial bladder carcinoma. Eur Urol. 2002 August; 42(2):167-74).

Following resection and first immediate treatment patients need to be stratified by their risk for tumor progression and recurrence:

Patients with low risk for disease progression/recurrence (30%)—need no further instillations.

Intermediate risk patients (40-50%)—usually receive 6 additional sessions of Mitomycin C (MMC) chemotherapy instillations.

High risk patients (20%)—are treated with 6 intravesical *Bacillus* Calmette-Guerin (BCG) instillations.

The efficacy of the current standard topical chemotherapy treatment for Superficial Bladder Cancer (intravesical instillation) is limited, because there is no control on the chemotherapy concentration and the time until it is expelled. In an attempt to prolong the standard treatment to two hours, some physicians dictate behavioral conditions to reduce acidity of the bladder, to reduce the volume of urine before the instillation and instill maximal concentration of chemotherapy dissolved in minimal volume of saline.

One object of the present invention is the provision of stable compositions comprising a lyophilized pharmaceutical composition comprising mitomycin C and a bulking agent and a hydrogel, more specifically thermoreversible hydrogel with the following properties: it is hydrophilic; it succeeds to deliver drug to the entire organ tissue at high enough drug concentration (above therapeutic threshold) in a homogeneous form; it is liquid at low temperatures such as at about 5° C. and semi-solid (does not flow) at body temperature, it is easily applied; it is biocompatible; it provides a continuous sustained release of a therapeutic agent; the rate of release of the therapeutic agent is determined by the concentration of the agent and the rate of degradation/dissolution of the hydrogel; and after the hydrogel degrades/dissolves, it is excreted from the body by the body's own natural processes.

A further object of the present invention is to provide a method for the treatment of cancer such as but not limiting to a urinary tract cancer using the compositions and the kit of the present invention. The compositions or the reconstituted components of the kit of the present invention may be applied topically or locally. Topical administration may include administration into a body space or cavity. Local administration may include administration to or into a tumor.

A further object of the present invention is to provide fast reconstitution of Mitomycin C in the thermoreversible hydrogel of the present invention to be mixed therein, thus facilitating the preparation of the compositions or reconstituted mixtures of the components of the kit.

A further object of the present invention is to provide compositions comprising a thermoreversible hydrogel and a lyophilized pharmaceutical composition comprising mitomycin C and a bulking agent having an increased storage stability.

A further object of the present invention is to provide compositions comprising a thermoreversible hydrogel and a lyophilized pharmaceutical composition comprising mitomycin C and a bulking agent having an increased solubility, reduced number of undissolved visible and subvisible particles and increased loading capacity.

A further object of the present invention is to provide compositions comprising a thermoreversible hydrogel and a lyophilized pharmaceutical composition comprising mitomycin C and a bulking agent wherein the amount of main impurities in the composition is reduced. The reduction of impurities inter alia provides enhanced storage stability of the compositions comprising a thermoreversible hydrogel and lyophilized Mitomycin. This enhanced stability of the inventive composition provides a prolonged period in which the composition can be used, e.g. administered or applied to a subject in need thereof.

When intended for instillation, it is further desirable that the composition exhibits a certain viscosity profile over different temperatures to allow instillation at low viscosities and viscosities high enough after instillation and higher temperatures to avoid outflow of the composition from the cavity and allow sufficient dwell-time within the cavity.

SUMMARY OF THE INVENTION

The current invention, as defined in the claims, is designed to meet the above objects. It comprises a series of systems that combine biocompatible mucoadhesive thermoreversible hydrogels and lyophilized pharmaceutical compositions, which are particularly suitable for the topical treatment of diseases that are focused in internal cavities.

In one aspect, the present invention pertains to a composition comprising a biocompatible mucoadhesive thermoreversible hydrogel comprising from about 15% to about 35% (w/w) of at least one reverse thermal gelation agent, from about 0.01% to about 5% (w/w) of a mucoadhesive polymer, from about 0% to about 2.5% (w/w) polyethylene glycol having an average molecular weight of from about 300 g/mol to about 1000 g/mol, and the balance water; and a therapeutically effective amount of a lyophilized pharmaceutical composition comprising mitomycin C and a bulking agent, wherein the bulking agent comprises urea.

In another aspect, the present invention pertains to a kit comprising components (a) and (b), wherein component (a) comprises a biocompatible mucoadhesive thermoreversible hydrogel comprising from about 15% to about 35% (w/w) of at least one reverse thermal gelation agent, from about 0.01% to about 5% (w/w) of a mucoadhesive polymer, from about 0% to about 2.5% (w/w) polyethylene glycol having an average molecular weight of from about 300 g/mol to about 1000 g/mol, and the balance water; and component (b) comprises therapeutically effective amount of a lyophilized pharmaceutical composition comprising mitomycin C and a bulking agent, wherein the bulking agent comprises urea.

In another aspect, the present invention pertains to a lyophilized pharmaceutical composition comprising mitomycin C and a bulking agent, wherein the bulking agent comprises urea, in combination with a biocompatible mucoadhesive thermoreversible hydrogel comprising from about 15% to about 35% (w/w) of at least one reverse thermal gelation agent, from about 0.01% to about 5% (w/w) of a mucoadhesive polymer, from about 0% to about 2.5% (w/w) polyethylene glycol having an average molecular weight of from about 300 g/mol to about 1000 g/mol, and the balance water; for use in the treatment of cancer such as urinary tract cancer.

In another aspect, the present invention pertains to the compositions of the present invention for use in the treatment of cancer such as urinary tract cancer.

In another aspect, the present invention pertains to a method for treating cancer such as urinary tract cancer, the method comprising administering the composition according to the present invention into a body cavity, such as the urinary tract, or locally to a subject in need thereof.

In another aspect, the present invention pertains to the kit of the present invention for use in the treatment of cancer such as urinary tract cancer.

In another aspect, the present invention pertains to a method for treating cancer such as urinary tract cancer, the method comprising providing component (a) and component (b) of the kit according to the present invention, reconstituting component (b) in component (a), and administering the reconstituted mixture of component (a) and component (b) into a body cavity, such as the urinary tract, or locally to a subject in need thereof.

In some aspects the cancer resides within the internal body cavity such as but not limited to the urinary tract, GI tract, or the intestine.

In other aspects, the invention pertains to a method of treating solid cancer by local administration, such as but not limiting to injecting into a solid tumor, of the composition according to the present invention to a subject in need thereof.

In other aspects, the invention pertains to a method of treating solid cancer by local administration, such as but not limiting to injecting into a solid tumor, the method comprising providing component (a) and component (b) of the kit according to the present invention, reconstituting component (b) in component (a), and locally administering the reconstituted mixture of component (a) and component (b) to the solid tumor in a subject in need thereof.

BRIEF DESCRIPTION OF THE FIGURES

FIG. 1: Mechanical resistance of composition G and E to a constant shear stress.

DETAILED DESCRIPTION OF THE PREFERRED EMBODIMENTS

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that described in the specification, but only as indicated in the accompanying claims, with the proper scope determined only by the broadest interpretation of said claims.

The following definitions are provided for the context of the present invention.

As used herein, the singular forms "a", "an", and "the" designate both the singular and the plural, unless expressly stated to designate the singular only.

As used herein, the term "comprising" is to be construed as encompassing both "including" and "consisting of", both meanings being specifically intended, and hence individually disclosed, embodiments according to the present invention.

The term "about" and the use of ranges in general, whether or not qualified by the term about, means that the number comprehended is not limited to the exact number set forth herein, and is intended to refer to ranges encompassed by the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10%, such as up to plus or minus 5%, of the particular term or value.

As used herein, the term "internal cavity" is used to describe parts in the body that are either accessible through an orifice for example but not limited to mouth, brain, lymph nodes, bladder, intestine, esophagus, rectum, lungs, vagina, stomach, renal pelvis, etc.—or by way of minimally invasive, surgery—e.g., pleura, abdomen, peritoneum, pelvis, etc. The definition includes artificially made or enlarged cavities in adipose tissues and fibrous capsules in internal organs such as the kidney, heart, intestine, etc. that are accessible by image guided laparoscopic techniques.

As used herein, the term "therapeutically effective amount" means that drug dosage, tissue concentration or plasma concentration in a subject, respectively, that provides the specific pharmacological effect for which the drug is administered in a subject in need of such treatment. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

The term "gel" or "hydrogel" as used herein refers to the biocompatible mucoadhesive thermoreversible hydrogel as defined in the present invention which is liquid at low temperatures (e.g. at about 5° C.) and solidifies at higher temperatures (at above 14° C.). The gel as described above is solid in vivo. The terms "solid" and "semi-solid" are used herein interchangeably. It means that a solid or semi-solid-material is a material which is not liquid and thus cannot flow.

The terms "drug", "active ingredient", "active pharmaceutical ingredient", "API", and "therapeutic agent" are used herein interchangeably.

Mitomycin C and MMC are used herein interchangeably.

The present invention pertains to compositions and kits comprising a biocompatible mucoadhesive thermoreversible hydrogel and a lyophilized pharmaceutical composition of Mitomycin C. It will be understood that all embodiments recited herein refer to both, the compositions and the kits according to the present invention including their uses in methods and treatments, unless explicitly stated otherwise.

As described above, one aspect of the present invention is a composition comprising a biocompatible mucoadhesive thermoreversible hydrogel comprising from about 15% to about 35% (w/w) of at least one reverse thermal gelation agent, from about 0.01% to about 5% (w/w) of a mucoadhesive polymer, from about 0% to about 2.5% (w/w) polyethylene glycol having an average molecular weight of from about 300 g/mol to about 1000 g/mol, and the balance water; and a therapeutically effective amount of a lyophilized pharmaceutical composition comprising mitomycin C and a bulking agent, wherein the bulking agent comprises urea.

A further aspect of the present invention is a kit comprising components (a) and (b), wherein component (a) comprises a biocompatible mucoadhesive thermoreversible hydrogel comprising from about 15% to about 35% (w/w) of at least one reverse thermal gelation agent, from about 0.01% to about 5% (w/w) of a mucoadhesive polymer, from about 0% to about 2.5% (w/w) polyethylene glycol having an average molecular weight of from about 300 g/mol to about 1000 g/mol, and the balance water; and component (b) comprises therapeutically effective amount of a lyophilized pharmaceutical composition comprising mitomycin C and a bulking agent, wherein the bulking agent comprises urea.

A further aspect of the present invention is a lyophilized pharmaceutical composition comprising mitomycin C and a bulking agent, wherein the bulking agent comprises urea in combination with a biocompatible mucoadhesive thermoreversible hydrogel comprising from about 15% to about 35% (w/w) of at least one reverse thermal gelation agent, from about 0.01% to about 5% (w/w) of a mucoadhesive polymer, from about 0% to about 2.5% (w/w) polyethylene glycol having an average molecular weight of from about 300 g/mol to about 1000 g/mol, and the balance water, for use in the treatment of cancer, such as internal body cavity cancer for example a urinary tract cancer, or be injected into a solid tumor.

Hence, the present invention provides a biocompatible mucoadhesive thermoreversible hydrogel having sustained-release properties, mixed with lyophilized mitomycin C (MMC). This hydrogel can be inserted into the body cavity such as but not limited to the urinary tract via a catheter or any other means. This hydrogel solidifies in the body cavity and form a drug reservoir at the destined treatment area such as the bladder or renal pelvis. The diffusion of MMC from the gel and the erosion of the gel by the urine deliver drug to the tissue—producing prolonged high topical drug concentration but low systemic exposure. Thus, the system increases bioavailability, reduces toxicity and improves treatment efficacy. Furthermore, loading the hydrogel with significant concentration of MMC and applying the hydrogel substantially directly over a tumor for a prolonged duration may ablate non-resected tumors that are in close contact with the hydrogel.

The present invention provides a design of such gel compositions that is based on the characteristics of the internal cavities to be treated and the specific requirements for said treatments in order to determine the required properties of hydrogel systems that can satisfy all these requirements.

The present invention also includes the use of the novel compositions and kits for producing medicaments which are intended for the treatment and/or prevention of disorders in humans. These medicaments can be combined with administering means, so that the compositions can be introduced in a minimally invasive manner into a body cavity and provide a prolonged and enhanced exposure of the cavity tissue to the drug, thus improving the treatment efficacy in terms of improved therapeutic effect of the drug and reduced tissue damage. The hydrogel of the present invention is biocompatible and dissolves in body fluids such as urine, serous fluids or lymphatic fluids, and then it is expelled from the body. The hydrogel does not block the cavity and biological fluids flow in the cavity and adapts to the volume and shape natural changes.

Mitomycin C (MMC)

The aim of the prolonged exposure of target tissue to MMC released from the hydrogel is to enhance the efficacy of the drug in topical treatment of that target tissue, while reducing potential systemic adverse effects to other organs. As a specific example, the aim of the prolonged exposure of cancer cells to the anticancer drug MMC released from the hydrogel is to enhance the efficacy of the drug in killing cancer cells and, therefore, potentially reduce the recurrence rate of cancer tumors, while reducing the systemic effect of chemotherapy on other parts of the patient body.

Depending on the type of the cancer and its locations, there may be limitations in terms of the amount of biocompatible mucoadhesive thermoreversible hydrogel comprising MMC which can be applied, e.g. due to limited spatial conditions. Furthermore, there may be cancer types which require a higher dosage of MMC applied via the biocompatible mucoadhesive thermoreversible hydrogel.

MMC can be present in the inventive compositions and kits in a broad range based on the total weight of the composition. In one embodiment, MMC is present in the inventive composition in a concentration of about 0.05 w/v.-% to about 1 w/v.-% based on the total weight of the composition. In another embodiment, MMC is present in the inventive kit in a concentration of about 0.05 w/v.-% to about 1 w/v.-% based on the total weight of component (a) and component (b) of the kit.

In cases where a high dosage of MMC is required, there is a substantial need to provide a high concentration of the MMC in the biocompatible mucoadhesive thermoreversible hydrogel. Thus there is a need to develop a pharmaceutical composition showing an enhanced solubility effect within the hydrogel i.e. a composition having an enhanced saturation concentration and a potential to effectively increase the MMC concentration in the gel.

In one embodiment, the saturation concentration of mitomycin C in the biocompatible mucoadhesive thermoreversible hydrogel is from about 4 mg/mL to about 7 mg/mL based on the total weight of the composition. Preferably, the saturation concentration of mitomycin C in the biocompatible mucoadhesive thermoreversible hydrogel is from about 5.2 mg/mL to about 7 mg/mL based on the total weight of the composition. In another embodiment, the saturation concentration of mitomycin C in the biocompatible mucoadhesive thermoreversible hydrogel is from about 4 mg/mL to about 7 mg/mL, preferably from about 5.2 mg/mL to about 7 mg/mL, based on the total weight of component (a) and component (b) after reconstitution of the kit according to the present invention.

The ratio MMC:Bulking Agent

Preferably, the active ingredient (MMC) is in lyophilized form. The active ingredient comprises crystalline and/or amorphous forms, or any mixture thereof.

In one embodiment, mitomycin C and the bulking agent are present in the lyophilized pharmaceutical composition in a ratio of from about 1:3 to about 1:20, such as about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, or about 1:20. Preferably, mitomycin C and the bulking agent are present in the lyophilized pharmaceutical composition in a ratio of from about 1:4 to about 1:15. More preferably, mitomycin C and the bulking agent are present in the lyophilized pharmaceutical composition in a ratio of from about 1:6 to about 1:10 e.g. from about 1:7 to about 1:9. Even more preferably, mitomycin C and the bulking agent are present in the lyophilized pharmaceutical composition in a ratio of about 1:8. It is to be understood that references to a ratio of MMC and the bulking agent refer to weight ratios.

The compositions and kits of the present invention comprise a lyophilized pharmaceutical composition comprising mitomycin C and a bulking agent, wherein the bulking agent comprises urea. Preferably, the bulking agent is urea.

In one embodiment, further APIs in addition to MMC may be present in the compositions or the kits of the present invention.

Among the drugs that can be administered topically and which may be further comprised in the compositions or the kits of the present invention are drugs that belong to the following families as described below,
1. Antineoplastic drugs
2. Chemotherapeutic agents
3. Anti-infective agents (e.g. Antimicrobial drugs, Antiparasitic agents, Antivirals)
4. Anti-inflammatory products
5. Drugs acting on the blood and blood forming organs (Antihemorrhagics, Antithrombotic agents, antianemic drugs
6. anti-cancer drugs
7. Anasthetic drugs
8. Immuno-therapy drugs
9. Vaccines
10. Live cells
11. Live organisms
12. Growth factors and substances to promote wound healing
13. Immunomodulators The present invention provides a biocompatible mucoadhesive thermoreversible hydrogel which releases MMC, either alone or in combination with other active ingredients (API), in a controlled fashion over a prolonged period. Such period can last for up to 30 hours.

Furthermore, the compositions of the present invention may provide particular release profiles of MMC. As a non-binding example, an average release rate of the active ingredient can vary between 80% in 3 hours and 80% in 24 hours. Preferably, 80% of MMC is released in about 3-12 hours. Still more preferably 80% of MMC is released in about 4-8 hours.

As standard, chemotherapy drugs are administered at a maximal concentration level that is tolerable by patients. A further improvement in efficacy can be gained by increasing the exposure time to chemotherapy drugs. This invention is designed to achieve this by increasing the dwell time as well as the tissue exposure of the active drug throughout the organ.

A longer exposure time of the API has distinct advantages and it is expected that a prolonged exposure with an API on use of a medicament with controlled release of the active ingredient(s) makes it possible to prolong substantially the time window in which improved therapy can be achieved. The use of the inventive medicinal forms with controlled release of MMC is expected to achieve substantially more constant drug levels and avoid the occurrence of level peaks, thus improving for example the therapeutic efficacy and reducing the frequency and intensity of unwanted side effects.

In addition, the use of the inventive compositions and kits allows the frequency of administration to be reduced and thus leads to improved acceptance and compliance by the patient.

It is expected as well that controlled-release of MMC prolongs exposure without the occurrence of an increase in side effects, an adverse effect on reliability and safety of therapies.

The Hydrogel:

The hydrogel comprised in the compositions and kits of the present invention comprises at least one reverse thermal gelation agent. Preferably, the reverse thermal gelation agent is a Poloxamer. Poloxamer designates a group of tri-block copolymers designated as PEG-PPG-PEG (PEG=Polyethylene glycol and PPG=Polypropylene glycol) that produce reverse thermal gelation compositions, i.e., with the characteristic that their viscosity increases with increasing temperature up to a point from which viscosity again decreases. In particular, Poloxamer 407 possesses a gelling temperature which is above 10° C. but below the human body temperature, i.e., 37° C. This characteristic may confer the ability of a composition containing the compound to be injected or infused in liquid state into a bodily inner cavity at a low temperature and, afterwards, as the composition warms, it solidifies into a semi solid gel, serving as a drug reservoir for optimal delivery to the inner wall of the body cavity.

The hydrogel of the present invention provides a homogeneous delivery, and continuous sustained release of therapeutic agents upon the inner surface of an internal body cavity.

In general, the hydrogel of the present invention can be applied, e.g. for topical treatment, in a variety of internal body cavities including the urinary bladder, mouth, nasal and paranasal sinus, gallbladder, esophagus, rectum, lungs, vagina, uterus, stomach, renal pelvis, pleura, abdomen, peritoneum, pelvis, liver, kidney, heart, intestine, brain, lymph nodes and vertebral column, etc. or even directly to a solid tumor by injection or any similar means.

Poloxamer 407 (PF-127) is a nonionic surfactant composed of polyoxyethylene-polyoxypropylene triblock copolymers. At low concentrations ($10^{-4}$-$10^{-5}$%) they form monomolecular micelles, but higher concentrations result in multimolecular aggregates consisting of a hydrophobic central core with their hydrophilic polyoxyethylene chains facing the external medium. Without wishing to be bound by any theory, the micellization occurs in dilute solutions of block copolymers in selected solvents above the critical micellar concentration, at a given temperature. At higher concentrations, above a critical gel concentration, the micelles can order into a lattice.

Commonly used poloxamers include Poloxamer 188 (F-68 grade), Poloxamer 237 (F-87 grade), Poloxamer 338 (F-108 grade) and Poloxamer 407 (F-127 grade) types, which are freely soluble in water. F-127 has a good solubilizing capacity, low toxicity and is, therefore, considered a good medium for drug delivery systems.

In one embodiment, the at least one Poloxamer is selected from Poloxamer 188, Poloxamer 338, and Poloxamer 407. Preferably, the at least one Poloxamer is Poloxamer 407.

The at least one reverse thermal gelation agent is comprised in the biocompatible mucoadhesive thermoreversible hydrogel in an amount of from about 15% to about 35% (w/w) based on the total weight of the biocompatible mucoadhesive thermoreversible hydrogel. In a preferred embodiment, the reverse thermal gelation agent is Poloxamer 407 and is comprised in the biocompatible mucoadhesive thermoreversible hydrogel in an amount of from about 15% to about 35% (w/w) based on the total weight of the biocompatible mucoadhesive thermoreversible hydrogel.

The compositions and kits of the present invention further comprise polyethylene glycol having an average molecular weight of from about 300 g/mol to about 1000 g/mol. In one embodiment, the polyethylene glycol is PEG-400 or PEG-800. Preferably the polyethylene glycol is PEG-400.

The polyethylene glycol having an average molecular weight of from about 300 g/mol to about 1000 g/mol is comprised in the biocompatible mucoadhesive thermoreversible hydrogel in an amount of from about 0% to about 2.5% (w/w) based on the total weight of the biocompatible mucoadhesive thermoreversible hydrogel. Preferably, the polyethylene glycol having an average molecular weight of from about 300 g/mol to about 1000 g/mol is comprised in the biocompatible mucoadhesive thermoreversible hydrogel in an amount of from about 0.1% to about 1.8% (w/w) based on the total weight of the biocompatible mucoadhesive thermoreversible hydrogel. In a preferred embodiment, the biocompatible mucoadhesive thermoreversible hydrogel comprises from about 0.1% to about 1.8% (w/w) PEG-400.

The compositions and kits of the present invention further comprise a mucoadhesive polymer.

In one embodiment, the mucoadhesive polymer is selected from the group consisting of cellulose, microcrystalline cellulose, cellulose derivatives, PVP, vinylpyrrolidone/vinyl acetate copolymer, polyethylene glycol, polyethylene oxide, polymethacrylates, polyvinyl alcohols (PVA), fats, and fatty acid derivatives, or any combination thereof. Preferably, the mucoadhesive polymer is a cellulose derivative. In one embodiment, the cellulose derivative is selected from the group consisting of alkylcelluloses, hydroxyalkylcelluloses, hydroxyalkylmethylcelluloses, carboxy-methylcelluloses, carbomers, alginates, and combinations thereof.

Preferably, the cellulose derivative is selected from the group consisting of hydroxypropyl methylcellulose (HPMC), hydroxy-propylcellulose (HPC), methylcellulose (MC), low-substituted hydroxypropylcellulose (L-HPC), ethylcellulose, and hydroxypropymethylcellulose acetate succinate (HPMCAS). More preferably, the cellulose derivative is hydroxypropyl methylcellulose (HPMC).

In one embodiment, the mucoadhesive polymer comprises hydroxypropyl methylcellulose (HPMC). Preferably, the mucoadhesive polymer is hydroxypropyl methylcellulose (HPMC).

The mucoadhesive polymer is comprised in the biocompatible mucoadhesive thermoreversible hydrogel in an amount of from about 0.01% to about 5% (w/w) based on the total weight of the biocompatible mucoadhesive thermoreversible hydrogel.

In one embodiment, the mucoadhesive polymer is comprised in the biocompatible mucoadhesive thermoreversible hydrogel in an amount of from about 0.01% to about 4.5% (w/w), such as from about 0.01% to about 4% (w/w), from about 0.01% to about 3.5% (w/w), from about 0.01% to about 3% (w/w), from about 0.01% to about 2.5% (w/w), from about 0.01% to about 2% (w/w), or from about 0.01% to about 1.5% (w/w), based on the total weight of the biocompatible mucoadhesive thermoreversible hydrogel. Preferably, the mucoadhesive polymer is comprised in the biocompatible mucoadhesive thermoreversible hydrogel in an amount of from about 0.01% to about 1% (w/w) based on the total weight of the biocompatible mucoadhesive thermoreversible hydrogel. More preferably, the mucoadhesive polymer is comprised in the biocompatible mucoadhesive thermoreversible hydrogel in an amount of from about 0.01% to about 0.5% (w/w) based on the total weight of the biocompatible mucoadhesive thermoreversible hydrogel. Even more preferably, the mucoadhesive polymer is comprised in the biocompatible mucoadhesive thermoreversible hydrogel in an amount of from about 0.01% to about 0.3% (w/w) based on the total weight of the biocompatible mucoadhesive thermoreversible hydrogel.

In a preferred embodiment, the biocompatible mucoadhesive thermoreversible hydrogel comprises from about 0.01% to about 0.5% (w/w), preferably from about 0.01% to about 0.3% (w/w), hydroxypropylmethylcellulose (HPMC).

In one preferred embodiment, the biocompatible mucoadhesive thermoreversible hydrogel comprises from about 15% to about 35% (w/w) of Poloxamer 407, from about 0.01% to about 5% hydroxypropylmethylcellulose (HPMC), from about 0% to about 2.5% PEG-400, and the balance water.

In another preferred embodiment, the biocompatible mucoadhesive thermoreversible hydrogel comprises from about 15% to about 35% (w/w) of Poloxamer 407, from about 0.01% to about 0.5% hydroxypropylmethylcellulose (HPMC), from about 0% to about 2.5% PEG-400, and the balance water.

In another preferred embodiment, the biocompatible mucoadhesive thermoreversible hydrogel comprises from about 20% to about 30% (w/w) of Poloxamer 407, from about 0.1% to about 0.3% hydroxypropylmethylcellulose (HPMC), from about 0.1% to about 1.8% PEG-400, and the balance water.

The compositions and kits of the present invention may be adapted for local administration such as direct injection or instillation. The compositions and kits of the present invention are preferably adapted for intravesical instillation.

According to one embodiment of the present invention, the hydrogel described herein may additionally comprise at least one ingredient selected from:
(a) thickening compounds;
(b) pH-modifying substances;
(c) solubilizing agents; and
(d) tight junction modifiers and permeability enhancers.

The thickening compounds are polycarbophil (polymer of acrylic acid crosslinked with divinyl glycol), hydroxypropylmethylcellulose (HPMC) and polyvinylpyrrolidone (PVP). It is likewise possible to employ other naturally, synthetic or partially synthetic polymers such as, for example methylcellulose (MC), hydroxy-propylcellulose (HPC), other hydroxyalkylcelluloses and hydroxyalkylmethylcelluloses, carboxy-methylcelluloses and salts thereof, polyacrylic acids, polymethacrylates, gelatin, carbopol, starch or starch derivatives, as well as gums like guar gum and xanthan gum.

The pH-modifying substances include acids, bases and buffer. Addition of these substances makes it possible to stabilize the API.

The solubilizing agents compounds preferably used are PEGs, DMSO, diethylene glycol monoethylether, and cyclodextrin.

Tight junction modifiers and permeability enhancers include DMSO, hydrogen peroxide, propylene glycol, oleic acid, cetyl alcohol, benzalkonium chloride, sodium lauryl sulphate, isopropyl myristate, Tween 80, dimethyl sulfoxide, dimethyl formamide, dimethyl acetamide, sodium lauroylsarcosinate, sorbitan monolaurate, methyl sulfonylmethane.

Release Rate of the MMC in the Body Cavity

The biocompatible mucoadhesive thermoreversible hydrogel according to the invention with controlled release of active ingredient preferably has an average release rate of 80% in the time interval between 3 and 24 hours (80% in 3 hours and 80% in 24 hours).

In a particularly preferred embodiment mitomycin C is released into an internal body cavity such as but not limiting to the urinary tract under the following conditions: at body temperature; at a pH in the range of about 4.5 to about 8.0, and at a rate of about 80% in a time range of about 3 to about 24 hours.

It should be emphasized that the composition of the invention with controlled release of an active ingredient refers to all compositions in which the release of the active ingredient is modified, in particular the release is significantly slower, in comparison to a rapid-release form of intravesical liquid solutions comprising MMC.

Preferably, Mitomycin C is in a lyophilized form. The lyophilized MMC can be presented in a crystalline form or in amorphous form or in any mixtures of crystalline and amorphous forms thereof.

According to one embodiment of the present invention provides compositions and kits that are intended to be used locally. Thus, it would be useful to have a device that allows such application of said pharmaceutical composition to a body organ through an orifice (either natural or artificial), so as to allow forming a drug reservoir in the body cavity with said hydrogel gel. Such composition will (i) allow the controlled release of the drug or drugs within the body cavity; (b) will enable the gradual dilution of the hydrogel; and, (c) expelled from the body in a reasonable period of time.

The composition of the present invention can, in addition to Mitomycin C (MMC), further comprise a variety of drugs for the more efficient treatment of cancer.

The Viscosity of the Composition

In one embodiment, the composition of the present invention has a viscosity of less than about 500 mPa·s at a temperature of about 4° C. to about 12° C. Preferably, the composition of the present invention has a viscosity of less than about 200 mPa·s at a temperature of about 4° C. to about 12° C.

In one embodiment, the composition of the present invention has a viscosity of about 50 mPa·s to about 1500 mPa·s at a temperature of about 4° C. to about 6° C. In one embodiment, the composition of the present invention has a viscosity of less than about 300 mPa·s at a temperature of about 4° C. to about 6° C. Preferably, the composition of the present invention has a viscosity of less than about 200 mPa·s at a temperature of about of about 4° C. to about 6° C. In one embodiment, the composition of the present invention has a viscosity of less than about 300 mPa·s at a temperature of about 5° C. Preferably, the composition of the present invention has a viscosity of less than about 200 mPa·s at a temperature of about 5° C.

In one embodiment, the composition of the present invention has a viscosity of less than about 1000 mPa·s at a temperature of about 13° C. to about 15° C. In one embodiment, the composition of the present invention has a viscosity of less than about 300 mPa·s at a temperature of about 13° C. to about 15° C. In one embodiment, the composition of the present invention has a viscosity of less than about 200 mPa·s at a temperature of about 13° C. to about 15° C. In one embodiment, the composition of the present invention has a viscosity of less than about 500 mPa·s, such as less than about 200 mPa·s, at a temperature of about 14° C.

In one embodiment, the composition of the present invention has a viscosity of about 3000 Pa·s to about 10000 Pa·s at a temperature of about 18° C. to about 20° C. In one embodiment, the composition of the present invention has a viscosity of about 3500 Pa·s to about 7000 Pa·s at a temperature of about 18° C. to about 20° C. In one embodiment, the composition of the present invention has a viscosity of about 3800 Pa·s to about 6500 Pa·s at a temperature of about 18° C. to about 20° C. In one embodiment, the composition of the present invention has a viscosity of about 4000 Pa·s to about 6000 Pa·s at a temperature of about 19° C.

In one embodiment, the biocompatible mucoadhesive thermoreversible hydrogel comprised in the kit of the present invention has a viscosity of less than about 500 mPa·s at a temperature of about 4° C. to about 12° C. upon reconstitution of component (b) in the hydrogel. Preferably, the biocompatible mucoadhesive thermoreversible hydrogel comprised in the kit of the present invention has a viscosity of less than about 200 mPa·s at a temperature of about 4° C. to about 12° C. upon reconstitution of component (b) in the hydrogel.

In one embodiment, the biocompatible mucoadhesive thermoreversible hydrogel comprised in the kit of the present invention has a viscosity of about 50 mPa·s to about 1500 mPa·s at a temperature of about 4° C. to about 6° C. upon reconstitution of component (b) in the hydrogel. In one embodiment, the biocompatible mucoadhesive thermoreversible hydrogel comprised in the kit of the present invention has a viscosity of less than about 300 mPa·s at a temperature of about 4° C. to about 6° C. upon reconstitution of component (b) in the hydrogel. In one embodiment, the biocompatible mucoadhesive thermoreversible hydrogel comprised in the kit of the present invention has a viscosity of less than about 200 mPa·s at a temperature of about 4° C. to about 6° C. upon reconstitution of component (b) in the hydrogel. In one embodiment, the biocompatible mucoadhesive thermoreversible hydrogel comprised in the kit of the present invention has a viscosity of less than about 300 mPa·s at a temperature of about 5° C. upon reconstitution of component (b) in the hydrogel. In one embodiment, the biocompatible mucoadhesive thermoreversible hydrogel comprised in the kit of the present invention has a viscosity of less than about 200 mPa·s at a temperature of about 5° C. upon reconstitution of component (b) in the hydrogel.

In one embodiment, the biocompatible mucoadhesive thermoreversible hydrogel comprised in the kit of the present invention has a viscosity of less than about 1000 mPa·s at a temperature of about 13° C. to about 15° C. upon reconstitution of component (b) in the hydrogel. In one embodiment, the biocompatible mucoadhesive thermoreversible hydrogel comprised in the kit of the present invention has a viscosity of less than about 300 mPa·s at a temperature of about 13° C. to about 15° C. upon reconstitution of component (b) in the hydrogel. In one embodiment, the biocompatible mucoadhesive thermoreversible hydrogel comprised in the kit of the present invention has a viscosity of less than about 200 mPa·s at a temperature of about 13° C. to about 15° C. upon reconstitution of component (b) in the hydrogel. In one embodiment, the biocompatible mucoadhesive thermoreversible hydrogel comprised in the kit of the present invention has a viscosity of less than about 500 mPa·s, such as less than about 200 mPa·s, at a temperature of about 14° C. upon reconstitution of component (b) in the hydrogel.

In one embodiment, the biocompatible mucoadhesive thermoreversible hydrogel comprised in the kit of the present invention has a viscosity of about 3000 Pa·s to about 10000 Pa·s at a temperature of about 18° C. to about 20° C. upon reconstitution of component (b) in the hydrogel. In one embodiment, the biocompatible mucoadhesive thermoreversible hydrogel comprised in the kit of the present invention has a viscosity of about 3500 Pa·s to about 7000 Pa·s at a temperature of about 18° C. to about 20° C. upon reconstitution of component (b) in the hydrogel. In one embodiment, the biocompatible mucoadhesive thermoreversible hydrogel comprised in the kit of the present invention has a viscosity of about 3800 Pa·s to about 6500 Pa·s at a temperature of about 18° C. to about 20° C. upon reconstitution of component (b) in the hydrogel. In one embodiment, the biocompatible mucoadhesive thermoreversible hydrogel comprised in the kit of the present invention has a viscosity of about 4000 Pa·s to about 6000 Pa·s at a temperature of about 19° C. upon reconstitution of component (b) in the hydrogel.

The viscosity of the biocompatible mucoadhesive thermoreversible hydrogel according to the present invention may be determined with conventional methods known in the art, such as using a Brookfield viscometer. For example, viscosities can be tested as a function of temperature using "Low Viscosity" (LV) and "Regular Viscosity" (RV) Brookfield Viscometers including spindle SC4-14, thermocouple, and small sample adaptor chamber SC4-6R(P). Viscosity in LV Brookfield viscometer can be measured using a spindle speed of 100 rpm or 200 rpm for temperatures below gelation point. Viscosity in RV Brookfield viscometer can be measured using a spindle speed of 0.1 rpm for temperatures above gelation point. Gelation point can be determined as the temperature at which a sharp increase of viscosity is observed.

Without wishing to be bound by any theory it is believed that a release of drug from the biocompatible mucoadhesive thermoreversible hydrogel occurs due to two phenomena that take place simultaneously after the gel is applied to the body: (1) Drug diffusion from the gel to the aqueous medium (e.g. urine); (2) Dissolution of the gel itself in the aqueous medium.

Again without wishing to be bound by any theory it is believed that in a non-limiting example of biocompatible mucoadhesive thermoreversible hydrogel in the context of the present invention, the hydrophilic character of the composition is an advantageous characteristic: It allows the polymer composition to gradually dissolve in the urine after the drug has been essentially released and the therapeutic session has been concluded without leaving foreign polymer composition residues inside the cavity, such as bladder.

The biocompatible mucoadhesive thermoreversible hydrogel comprised in the compositions and kits of the present invention has Reverse Thermal Gelation (RTG) property, thus can be injected as a free-flowing, low-viscosity liquid at low temperatures and forms a gel upon exposure to body temperature. The compositions and kits comprising a biocompatible mucoadhesive thermoreversible hydrogel and MMC present excellent rheology properties, high bioadhesive capabilities and high therapeutic efficacy.

Gel Point

The gelation temperature (gel point) is one parameter in the design of the composition. It should be such to allow delivering of the composition of the target tissue, enabling mixing of component (a) with (b) prior to instillation and solidification following administration. Gelation temperature may also be connected to the strength of the hydrogel and dissolution rate and therefore should be such that is required for extended exposure.

Flexibility of the hydrogel is required to enable to adapt to volume and shape and natural changes through cycles of enlargement/reduction or flexing of muscles. For example, the volume of the bladder when the composition of the present invention is instilled is 100 ml, and when it is naturally filled with urine, it can grow to 300 ml and even more. The present invention's compositions are designed to withstand such cycles of expansion and collapse by physical strength deriving from the high viscosity at body temperature (i.e., 4000 Pa·s to about 6000 Pa·s).

Solubility

The inventors surprisingly found that when the bulking agent of the lyophilized pharmaceutical composition comprising MMC comprises urea, a higher saturation concentration of MMC in the biocompatible mucoadhesive thermoreversible hydrogel can be obtained.

It is desirable that the compositions and the reconstituted mixture of components (a) and (b) of the kit according to the present invention have a better solubility without undissolved visible particles and low amount of subvisible particles. Without wishing to be bound by any theory, the inventors believe that compositions and reconstituted mixtures according to the present invention which have a reduced number of visible and subvisible particles result in a hydrogel which has a higher homogeneity and higher efficacy.

The inventors surprisingly found that the biocompatible mucoadhesive thermoreversible hydrogel together with the lyophilized pharmaceutical composition comprising urea as bulking agent according to the present invention result in hydrogels having a significantly reduced number of undissolved visible and subvisible particles. Visible particles according to the present invention are particles above 100 µm. Subvisible particles according to the present invention is to be understood as particles having a size in the range of 1 µm to 100 µm. The number of subvisible particles can be determined by any conventional means applied in the art, such as by flow imaging microscopy. It is believed that by using urea as bulking agent the number of visible and subvisible particles can be significantly reduced as compared to other bulking agents such as mannitol.

Preferably, the composition according to the present invention has not more than 10,000 subvisible particles of above 10 µm per ml as determined by flow imaging microscopy, preferably not more than 9000 subvisible particles of above 10 µm per ml, more preferably not more than 8000 subvisible particles of above 10 µm per ml.

Preferably, the composition according to the present invention has not more than 5000 subvisible particles of above 20 µm per ml as determined by flow imaging microscopy, preferably not more than 3000 subvisible particles of above 20 µm per ml, more preferably not more than 2000 subvisible particles of above 20 µm per ml.

Preferably, the composition according to the present invention has not more than 100 subvisible particles of above 50 µm per ml as determined by flow imaging microscopy, preferably not more than 80 subvisible particles of above 50 µm per ml, more preferably not more than 60 subvisible particles of above 50 µm per ml.

More preferably, the composition according to the present invention has not more than 50 particles of above 100 µm per ml as determined by flow imaging microscopy, preferably not more than 30 particles of above 100 µm per ml, more preferably not more than 20 particles of above 100 µm per ml.

Preferably, when component (b) is reconstituted in component (a) of the kit according to the present invention, the reconstituted mixture has not more than 10,000 subvisible particles of above 10 µm per ml as determined by flow imaging microscopy, preferably not more than 9000 subvisible particles of above 10 μm per ml, more preferably not more than 8000 subvisible particles of above 10 μm per ml.

Preferably, when component (b) is reconstituted in component (a) of the kit according to the present invention, the reconstituted mixture has not more than 5000 subvisible particles of above 20 μm per ml as determined by flow imaging microscopy, preferably not more than 3000 subvisible particles of above 20 μm per ml, more preferably not more than 2000 subvisible particles of above 20 μm per ml.

Preferably, when component (b) is reconstituted in component (a) of the kit according to the present invention, the reconstituted mixture has not more than 100 subvisible particles of above 50 μm per ml as determined by flow imaging microscopy, preferably not more than 80 subvisible particles of above 50 μm per ml, more preferably not more than 60 subvisible particles of above 50 μm per ml.

More preferably, when component (b) is reconstituted in component (a) of the kit according to the present invention, the reconstituted mixture has not more than 50 particles of above 100 μm per ml as determined by flow imaging microscopy, preferably not more than 30 particles of above 100 μm per ml, more preferably not more than 20 particles of above 100 μm per ml.

The present invention also includes the use of the novel compositions and kits for producing medicaments which are intended for the treatment and/or prevention of disorders in humans.

In one embodiment, the compositions and kits according to the present invention are for use in the treatment of urinary tract cancer.

In one embodiment, the present invention provides a method for treating urinary tract cancer, the method comprising administering the composition of the present invention into the urinary tract of a subject in need thereof.

In one embodiment, administering comprises introducing the composition of the present invention into the internal body cavity of the urinary tract, applying said composition to at least part of the internal surface of the internal body cavity of the urinary tract, causing said composition to adhere to the internal surface of the internal body cavity of the urinary tract.

In one embodiment, the present invention provides a method for treating urinary tract cancer, the method comprising providing component (a) and component (b) of the kit of the present invention, reconstituting component (b) in component (a), and administering the reconstituted mixture of component (a) and component (b) into the urinary tract of a subject in need thereof.

The inventors surprisingly found that when the bulking agent of the lyophilized pharmaceutical composition of component (b) of the kit of the present invention comprises urea rapid reconstitution of component (a) and (b) can be provided. That means, reconstituting component (b) in component (a) only takes 15 minutes or less, such as 10 minutes or less, preferably 7 minutes or less, and more preferably 5 minutes or less. Preferably, component (b) is completely dissolved in component (a) in 10 minutes or less, more preferably in 7 minutes or less, and even more preferably in 5 minutes or less.

It is still further believed that the compositions of the present invention have superior stability and less degradation products. The same applies for the kit according to the present invention after reconstituting components (a) and (b).

It is furthermore desirable that the reconstituted mixture of components (a) and (b) is stable and can be stored for a certain period of time prior to administration to the patient.

The inventors surprisingly found that when the bulking agent of the lyophilized pharmaceutical composition comprising MMC comprises urea, the storage stability is increased after reconstitution of components (a) and (b) and the reconstituted mixture can be stored and used longer. Thus, the compositions according to the present invention likewise exhibit an increased storage stability. In this respect, the inventors surprisingly found that when the bulking agent of the lyophilized pharmaceutical composition comprises urea, the amount of impurities can be reduced as compared to other bulking agents such as mannitol. In one embodiment, the compositions and reconstituted mixture of components (a) and (b) of the kit according to the present invention can be stored up to 48 h, up to 36 h or up to 24 h.

In one embodiment, the impurity is selected from 1,2-trans-1-hydroxy-2,7-diaminomitosene, 1,2-cis-1-hydroxy-2,7-diaminomitosene, or a combination thereof. In one embodiment, when present, each of these compounds is present in the composition in an amount of less than 0.5% w/w, preferably less than 0.1% w/w. In one embodiment, 1,2-trans-1-hydroxy-2,7-diaminomitosene and/or 1,2-cis-1-hydroxy-2,7-diaminomitosene, when present, is present in the reconstituted mixture of component (a) and component (b) in an amount of less than 0.5% w/w, preferably less than 0.1% w/w directly after reconstitution (T=0 h). In one embodiment, 1,2-trans-1-hydroxy-2,7-diaminomitosene and/or 1,2-cis-1-hydroxy-2,7-diaminomitosene, when present, is present in the reconstituted mixture of component (a) and component (b) in an amount of less than 0.5% w/w after 8 h following reconstitution, and preferably 1.0% after 24 h following reconstitution. The impurities may be determined by any suitable method known in the art such as high-performance liquid chromatography (HPLC).

In one embodiment, administering comprises introducing the reconstituted mixture of component (a) and component (b) into the internal body cavity of the urinary tract, applying said reconstituted mixture of component (a) and component (b) to at least part of the internal surface of the internal body cavity of the urinary tract, causing said reconstituted mixture of component (a) and component (b) to adhere to the internal surface of the internal body cavity of the urinary tract.

Preferably, the internal body cavity of the urinary tract is the bladder or the upper tract.

Preferably, the urinary tract cancer is bladder cancer or upper tract urothelial cancer (UTUC).

The non-limiting examples presented below illustrate the versatility that is provided by the diverse compositions, that allows its engineering to render different release profiles, flow characteristics, instillation temperatures, coating layer thickness and additional features as required by the specific treatment to be applied upon an internal cavity.

In one embodiment, the inventive compositions or mixture of reconstituted components (a) and (b) of the inventive kit is inserted into the essentially empty bladder using a catheter. The composition is inserted at low temperature in the range of about 1° C. to about 18° C., where the material viscosity is low enough to be able to flow freely into the bladder, more preferable at the temp in the range of about 10° C. to about 18° C. As the liquid material flows into the bladder it is naturally heated by the body temperature and eventually it reached that temperature. When the composition's temperature reaches the gelation temperature—it is passes from the liquid phase to viscous gel phase. The present invention's method is designed to ensure that the composition will deliver an effective amount of active to the tissue.

The versatility of the inventive composition and the ability to control its physicochemical properties may allow the incorporation and optimize sustained-release dosing of additional active ingredients that may be desired in a chemotherapy treatment, including the reduction of pain, avoidance of inflammation and other undesired effects. Thus, besides the active ingredient MMC that serve as anti-cancer agent, other drugs can be incorporated in the gel composition, among them anesthetic drugs (e.g., lidocaine), coagulants (e.g., proconvertin) anticoagulants (like heparin), anti-inflammatory drugs (steroidal and non-steroidal) and others, according to the medical requirements for patients suffering of SBC utilizing the effect of gradual release of the diverse active components for an optimal treatment.

The compositions and kits of the present invention comprise MMC as active ingredient. Specifically, the anti-cancer drug mitomycin C (MMC) has been experimentally utilized in in vitro settings and applied on the internal bladder wall of animal specimens and in vivo tests. MMC with or without another API is released in a controlled manner and the residence time inside the bladder is in the order of up to 30 hours instead of the accustomed 1-2 hours (until micturition).

The present invention, as described above and defined in the claims, is designed to meet requirements of pharmaceutical compositions' properties desirable for delivery of MMC to an internal body cavity. The properties of the compositions of the invention are:
(a) overcome/withstand the highly liquid environment within the cavity which greatly affect the gel's ability to sustain drug delivery for a significant duration (gel dissolution rate should be as low as possible in order to increase treatment duration and hence treatment efficacy);
(b) gelate at a desirable temperature (e.g. internal body temperature), which allows for simple instillation without risk of syringe/medical device clogging;
(c) possess a viscosity that is low enough to enable catheter-delivered gel instillation and high enough to allow a long residence (dwell time is longer) within the cavity
(d) possess sufficient mucoadhesiveness to enable increased local drug delivery despite the highly liquid environment within the urinary tract, and without being too viscous to allow catheter-assisted instillation;
(e) be stable over a duration long enough to effectively deliver drug to the target area and a long in-use period.

It will be obvious for a person skilled in the art that the embodiments disclosed herein only depict examples of a plurality of possibilities. Hence, the embodiments shown here should not be understood to form a limitation of these features and configurations. Any possible combination and configuration of the described features can be chosen according to the scope of the invention. All embodiments and preferred embodiments described herein in connection with one particular aspect of the invention (e.g. the inventive composition) shall likewise apply to all other aspects of the present inventions such as kits, pharmaceutical compositions, uses and methods according to the present invention.

The present invention will be further illustrated by the following examples, which shall not be construed as limiting.

EXAMPLES

In the following examples, formulations comprising a thermoreversible hydrogel and i) a lyophilized composition comprising MMC and urea as bulking agent or ii) a lyophilized composition comprising MMC and mannitol as bulking agent, were tested.

The thermoreversible hydrogel used in the present examples comprised Poloxamer 407 (PF-127) (27.0% w/w); polyethylene glycol, average MW=400 (PEG-400) (1.0% w/w); hydroxypropylmethyl cellulose (HPMC) (0.2% w/w) with the remainder (71.8%) double distilled water.

The lyophilized composition comprising MMC and mannitol was composed of 1:2 w/w MMC:mannitol, commercially available e.g. from Accord Healthcare.

The lyophilized composition comprising MMC and urea was manufactured according to the process described in patent application US 2016/256391 with the following mitomycin/urea ratios:
a) 1:4 w/w MMC:Urea
b) 1:5 w/w MMC:Urea
c) 1:6 w/w MMC:Urea
d) 1:8 w/w MMC:Urea
e) 1:10 w/w MMC:Urea
f) 1:15 w/w MMC:Urea The lyophilized compositions comprising MMC which were reconstituted in the thermoreversible hydrogel are summarized in Table 1.

TABLE 1

| | Lyophilized Compositions | | | | | | |
|---|---|---|---|---|---|---|---|
| Composition | A (ref.) | B | C | D | E | F | G |
| Ratio of MMC:bulking agent | 1:2 MMC:mannitol | 1:4 MMC:urea | 1:5 MMC:urea | 1:6 MMC:urea | 1:8 MMC:urea | 1:10 MMC:urea | 1:15 MMC:urea |

The MMC concentration in the hydrogel was 4 mg/mL unless otherwise explicitly indicted in the Examples below. In the following examples, unless otherwise explicitly indicted, the lyophilized composition comprising MMC was reconstituted in thermoreversible hydrogel according to the following protocol: 2 ml of water for injection was mixed with 4 ml of hydrogel as prewetting solution, the lyophilized composition comprising MMC was mixed with the prewetting solution, followed by addition of 14 mL hydrogel to the mixture.

Example 1a: Visible Particles after Reconstitution

The visible particles were tested for composition A (ref.), E and F following mixing with hydrogel. The number of visible particles was determined by FlowCam® Instrument (Dynamic Image Analysis). The samples for FlowCam® Instrument testing were diluted 1:1 with water prior to testing. The results are summarized in Table 2.

TABLE 2

Number of visible particles in composition

|  | Composition | | |
| --- | --- | --- | --- |
|  | A (ref.) | E | F |
| Visible particles | About 10 visible particles | No visible particles | No visible particles |

As is shown in Table 2, compositions E and F according to the present invention including urea as bulking agent exhibited no visible particles compared to composition A.

Example 1b: Visible Particles During Holding Time in −20° C.

The visible particles following mixing with hydrogel were tested for composition A and E following storage up to 9 days at (−20° C.). The number of visible particles was determined by visual observation. The results are summarized in Table 3.

TABLE 3

Visible particles after storage in −20° C.

Visible particles after storage at −20deg

| Composition | 24 h | 2 days | 3 days | 4 days | 9 days |
| --- | --- | --- | --- | --- | --- |
| A | Clear liquid, contain few visible particles | NT | Clear liquid, contain few visible particles | Turbid liquid due to many visible particles | NT |
| E | Clear liquid, no visible particles | Clear liquid, no visible particles | NT | Clear liquid, no visible particles | Clear liquid, no visible particles |

NT: Not tested

As is shown in Table 3, composition E according to the present invention including urea as bulking agent exhibited no visible particles after storage at −20° C. for at least 9 days compared to composition A including mannitol as bulking agent for which many visible particles were observed following 4 days of storage.

It is clearly observed in respect to solubility and visible particles that composition E provides longer in-use holding time compared to composition A. Thus, the storage stability is significantly increasing after reconstitution and the composition can be stored and used longer.

Example 2: Subvisible Particles

The number of subvisible particles and their distribution were tested for composition A (ref) as well as composition E and G according to the present invention. The number and distribution of subvisible particles was determined by Flow-Cam® Instrument (Dynamic Image Analysis). The samples were diluted ×2 prior examination. The results are summarized in Table 4.

TABLE 4

Number of subvisible particles

|  |  | Composition | | |
| --- | --- | --- | --- | --- |
|  |  | A (ref.) | E | G |
| Number of subvisible particles [particles/ml] | above 10 μm | 365,692 | 6,067 | 4,361 |
|  | above 20 μm | 73,129 | 1,391 | 1,423 |
|  | above 50 μm | 890 | 24 | 5 |
|  | Sticks* | 569,291 | 10,830 | 7,807 |

*Sticks are particles with an aspect ratio (ratio of diameters) from 0.01 to 0.74 and diameter (area based diameter) from 7 to 500 μm.

As is shown in Table 4, compositions E and G according to the present invention including urea as bulking agent exhibit significantly less subvisible particles compared to composition A including mannitol as bulking agent.

Example 3: Reconstitution Time

Lyophilized compositions must be reconstituted back into solution prior to patient administration and in this regard long reconstitution times are not ideal. Reconstitution time is very important parameter in development of lyophilized drugs. Lyophilized composition comprising MMC was reconstituted in thermoreversible hydrogel according to the following protocol: 2 ml of water for injection was mixed with 4 ml of hydrogel as prewetting solution, the lyophilized composition comprising MMC was mixed with the prewetting solution, followed by addition of 14 mL hydrogel to the mixture. The reconstitution time for composition preparation was estimated as the time when substantially all mitomycin was dissolved within the gel.

TABLE 5

Reconstitution time

|  | Composition | |
| --- | --- | --- |
|  | A | E |
| Reconstitution time | 30 minutes | Less than 5 min |

As shown in Table 5, Composition E comprising urea at 1:8 (MMC:Urea) exhibits significantly shorter reconstitution time. The significant short reconstitution time is very important parameter that simplifies the usage of the product.

Example 4: Evaluation of Impurities

Impurities of composition A (ref.) and compositions E and G according to the present invention were determined.

Impurities 1,2-trans-1-hydroxy-2,7-diaminomitosene and 1,2-cis-1-hydroxy-2,7-diaminomitosene are commonly known impurities of mitomycin, evolving in polar solvents.

Impurities 1,2-trans-1-hydroxy-2,7-diaminomitosene and 1,2-cis-1-hydroxy-2,7-diaminomitosene were tested in compositions A (ref.) and E according to the present invention at a mitomycin concentration of 4 mg/mL, immediately after composition reconstitution (T=0) and following a storage at 30° C. for 8 h (T=8 h) and 24 h (T=24 h). Lyophilized composition comprising MMC was reconstituted in thermoreversible hydrogel according to the following protocol: 2 ml of water for injection was mixed with 4 ml of hydrogel as prewetting solution, the lyophilized composition comprising MMC was mixed with the prewetting solution, followed by addition of 14 mL hydrogel to the mixture. Impurities were tested using high-performance liquid chromatography (HPLC). Results are summarized in Table 6 and Table 7, respectively.

TABLE 6

Impurities in compositions A and E, 4 mg/ml MMC at T = 0

| | Composition | | | |
|---|---|---|---|---|
| | A | | E | |
| | Batch 1 | Batch 2 | Batch 1 | Batch 2 |
| 1,2-trans-1-hydroxy-2,7-diaminomitosene | 0.5% w/w | 0.6% w/w | <0.1% w/w | <0.1% w/w |
| 1,2-cis-1-hydroxy-2,7-diaminomitosene | 0.5% w/w | 0.7% w/w | <0.1% w/w | <0.1% w/w |

TABLE 7

Impurities in compositions A and E, 4 mg/ml MMC after 8 h and 24 h storage at 30° C.

| | Composition | | | |
|---|---|---|---|---|
| | A (ref.) | | E | |
| Storage time | T = 8 h | T = 24 h | T = 8 h | T = 24 h |
| 1,2-trans-1-hydroxy-2,7-diaminomitosene | 0.6% w/w | 1.3% w/w | 0.2% w/w | 0.6% w/w |
| 1,2-cis-1-hydroxy-2,7-diaminomitosene | 0.5% w/w | 1.5% w/w | 0.2% w/w | 0.6% w/w |

As shown in Table 6 and Table 7, the inventive composition E comprising urea as bulking agent exhibits significantly less impurities at T=0, T=8 h and T=24 h after reconstitution compared to composition A including mannitol as bulking agent. Particularly, the amount of impurities 1,2-trans-1-hydroxy-2,7-diaminomitosene and 1,2-cis-1-hydroxy-2,7-diaminomitosene is significantly lower in the composition according to the present invention. Thus, the storage stability is significantly increased after reconstitution and the reconstituted mixture can be stored and used longer. The longer stability following reconstitution is an important parameter that simplifies the usage of the product.

Impurities 1,2-trans-1-hydroxy-2,7-diaminomitosene and 1,2-cis-1-hydroxy-2,7-diaminomitosene were further determined in compositions A (ref.), E and G according to the present invention at final MMC concentration 1.33 mg/mL immediately after composition reconstitution (T=0) and following storage in 30° C. for 8 h (T=8 h) and 24 h (T=24 h) and 48 h (T=48 h). Lyophilized composition comprising MMC was reconstituted in thermoreversible hydrogel according to the following protocol: 2 ml of water for injection was mixed with 4 ml of hydrogel as prewetting solution, the lyophilized composition comprising MMC was mixed with the prewetting solution, followed by addition of 14 mL hydrogel to the mixture. Impurities were tested using high-performance liquid chromatography (HPLC). Results are summarized in Table 8.

TABLE 8

Impurities in composition A, E, and G, 1.33 mg/ml MMC at T = 0 and storage of 24 h and 48 h at 30° C.

| Composition | A | | | E | | | G | | |
|---|---|---|---|---|---|---|---|---|---|
| | 0 | 24 h | 48 h | 0 | 24 h | 48 h | 0 | 24 h | 48 h |
| 1,2-trans-1-hydroxy-2,7-diaminomitosene | 0.8% w/w | 1.5% w/w | 2.1% w/w | <0.1% w/w | 0.7% w/w | 1.4% w/w | <0.1% w/w | 0.7% w/w | 1.3% w/w |
| 1,2-cis-1-hydroxy-2,7-diaminomitosene | 0.7% w/w | 1.7% w/w | 1.9% w/w | <0.1% w/w | 0.8% w/w | 1.5% w/w | <0.1% w/w | 0.8% w/w | 1.6% w/w |

As shown in Table 8, the inventive compositions E and G exhibit less impurities at T=0, T=24 h and T=48 h after reconstitution compared to composition A when composition is prepared at MMC concentration of 1.33 mg/ml. Particularly, the amount of impurities 1,2-trans-1-hydroxy-2,7-diaminomitosene and 1,2-cis-1-hydroxy-2,7-diaminomitosene is significantly lower. Thus, the storage stability could be significantly increased be replacing mannitol with urea.

Example 5: Viscosity and Gelation Temperature

Viscosities and gelation temperature of compositions comprising urea as bulking agent according to the present invention were determined and compared to composition A (ref) comprising mannitol.

The viscosities of the tested compositions were tested as a function of temperature using "Low Viscosity" (LV) and "Regular Viscosity" (RV) Brookfield Viscometers including spindle SC4-14, thermocouple, and small sample adaptor chamber SC4-6R(P). Viscosity in LV Brookfield viscometer was measured using spindle speed of 100 rpm or 200 rpm for temperatures below gelation point. Viscosity in RV Brookfield viscometer was measured using spindle speed of 0.1 rpm for temperatures above gelation point. Gelation point was determined as the temperature at which sharp increase of viscosity is observed.

The viscosities determined at 14° C. and 19° C. and the gelation temperature of composition A (ref.) and compositions B to G are summarized in Table 9.

TABLE 9

Viscosities at 14° C. and 19° C. and the gelation temperature

| Composition | Viscosity at 14° C. [mPa · s] | Viscosity at 19° C. [mPa · s] | Gelation point [° C.] |
| --- | --- | --- | --- |
| A (ref.) | 223 | $6.7 \times 10^6$ | 16.0 |
| B | 115 | $5.7 \times 10^6$ | 17.5 |
| C | 109 | $5.2 \times 10^6$ | 17.5 |
| D | 120 | $5.3 \times 10^6$ | 17.5 |
| E | 111 | $5.1 \times 10^6$ | 17.5 |
| F | 100 | $4.6 \times 10^6$ | 18.0 |
| G | 83 | $3.7 \times 10^6$ | 19.0 |

As shown in Table 9, the viscosities and gelation point of compositions A, and B to F are in the range of 4600 Pa·s and 5700 Pa·s. The inventors believe that a lower gelation point and higher viscosity contributes to longer dwell time and extended exposure to the active ingredient.

Example 6: Mechanical Properties

The mechanical resistance to constant shear stress in an aqueous environment, was determined for compositions G and E by flow peak hold test. This test was developed to simulate the stress conditions in urinary system and predict the comparative behaviour of different compositions within the urinary system. Composition exhibiting mechanical failure at longer stress time is expected to be favourable to be used in the urine system and provide longer exposure time.

The flow peak hold test under constant shear stress of 250 Pa and an axial force of 1N as a function of time was applied using DHR-1 Rheometer (TA-Instruments).

As shown in FIG. 1, the mechanical resistance of composition E to a constant shear stress in an aqueous environment is higher (i.e. longer time required to mechanical failure indicated by sharp decrease in viscosity) than that of composition G. Thus, it was surprisingly found that a ratio of 1:8 MMC:urea (composition E) yields excellent mechanical properties of the hydrogel.

Example 7: Solubility in Hydrogel

Solubility of lyophilized MMC, containing urea or mannitol, in the hydrogel was tested. The lyophilized MMC was compounded in excess into the hydrogel (lyophilized MMC: hydrogel at a weight ratio of 1:2) and stirred for 1 hour at 2-8° C. A particle free portion of the samples, obtained by centrifugation followed by filtration via 0.45 μm filter, was analysed by HPLC. The results are summarized in Table 10.

TABLE 10

MMC solubility in hydrogel

| Formulation | Avg. MMC conc., mg/ml |
| --- | --- |
| A | 5.0 |
| E | 6.2 |

As shown in Table 10 the inventive composition E including urea as bulking agent exhibits higher MMC solubility in thermoreversible hydrogel compared to composition A having mannitol as bulking agent.

The invention claimed is:

1. A kit comprising:
   (a) a biocompatible thermoreversible hydrogel comprising
      from 15% to 35% (w/w) of Poloxamer 407 based on a total weight of the biocompatible thermoreversible hydrogel,
      from 0.01% to 0.3% (w/w) of hydroxypropylmethylcellulose based on a total weight of the biocompatible thermoreversible hydrogel, and
      water; and
   (b) a lyophilized composition comprising mitomycin C and a bulking agent,
   wherein the bulking agent is urea.

2. The kit according to claim 1, wherein the biocompatible thermoreversible hydrogel further comprises from 0.1% to 1.8% (w/w) of PEG-400 based on a total weight of the biocompatible thermoreversible hydrogel.

3. The kit according to claim 2, wherein mitomycin C and the bulking agent are present in a ratio of about 1:8 in the lyophilized composition.

4. The kit according to claim 2, wherein mitomycin C and the bulking agent are present in a ratio of about 1:7 to about 1:14 in the lyophilized composition.

5. The kit according to claim 1, wherein mitomycin C and the bulking agent are present in a ratio of about 1:8 in the lyophilized composition.

6. The kit according to claim 1, wherein mitomycin C and the bulking agent are present in a ratio of about 1:7 to about 1:14 in the lyophilized composition.

* * * * *